United States Patent [19]
Zinreich et al.

[11] Patent Number: 5,628,733
[45] Date of Patent: May 13, 1997

[54] SURGICAL DRAIN

[75] Inventors: S. James Zinreich; Eva S. Zinreich, both of Owings Mills; Douglas E. Mattox, Ruxton, all of Md.

[73] Assignee: IZI Corporation, Owings Mills, Md.

[21] Appl. No.: 205,517

[22] Filed: Mar. 3, 1994

[51] Int. Cl.⁶ ........................................ A61M 25/00
[52] U.S. Cl. ........................................ 604/267
[58] Field of Search ........................... 604/267, 280, 604/264, 96; 606/191–197

[56] References Cited

U.S. PATENT DOCUMENTS

| | | | |
|---|---|---|---|
| 396,754 | 1/1889 | Mayfield | 604/267 |
| 564,581 | 7/1896 | Baker | 604/267 |
| 878,199 | 2/1908 | Freeman | 604/267 |
| 918,437 | 4/1909 | Genung | 604/267 |
| 954,494 | 4/1910 | Andrews | 604/267 |
| 1,008,128 | 11/1911 | Flagg | 604/267 |
| 1,112,982 | 10/1914 | Conine | 604/267 |
| 2,012,363 | 8/1935 | Vogel | 604/267 |
| 2,073,069 | 3/1937 | Lee | 604/267 |
| 2,137,635 | 11/1938 | Tyler | 604/267 |
| 2,571,207 | 10/1951 | Cox | 604/267 |
| 3,308,825 | 3/1967 | Cruse | |
| 3,595,241 | 7/1971 | Sheridan | 604/267 |
| 3,703,899 | 11/1972 | Calinog | 604/267 |
| 3,758,950 | 9/1973 | Krouzian | |
| 3,863,641 | 2/1975 | Popa | 604/267 |
| 4,158,916 | 6/1979 | Adler | |
| 4,228,802 | 10/1980 | Trott | 604/267 |
| 4,451,257 | 5/1984 | Atchley | |
| 4,767,404 | 8/1988 | Renton | |
| 4,867,747 | 9/1989 | Yarger | |
| 5,030,213 | 7/1991 | Rumberger et al. | 604/267 |
| 5,375,589 | 12/1994 | Bhatta | 604/267 |

*Primary Examiner*—Manuel Mendez
*Attorney, Agent, or Firm*—Lyon & Lyon

[57] ABSTRACT

A surgical drain for draining wounds is disclosed. The drain has a tube-like body forming a lumen. The body of the drain includes a plurality of perforations therein. The drain also has a plunger for removing debris from the lumen and perforations of the drain. The plunger has a scraper, a line and a handle. The scraper of the plunger is generally located in the lumen of the body. The handle of the plunger is generally located so as to be accessible to a user. The line of the plunger generally extends through the lumen and connects the scraper and handle. The drain may have more than one plunger.

7 Claims, 3 Drawing Sheets

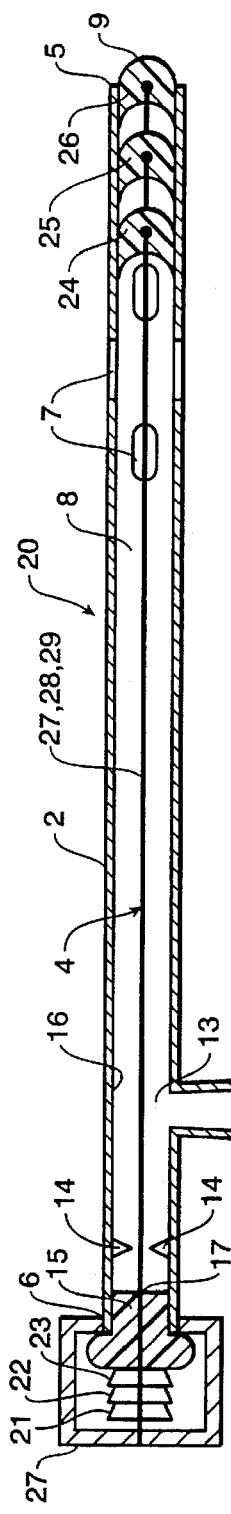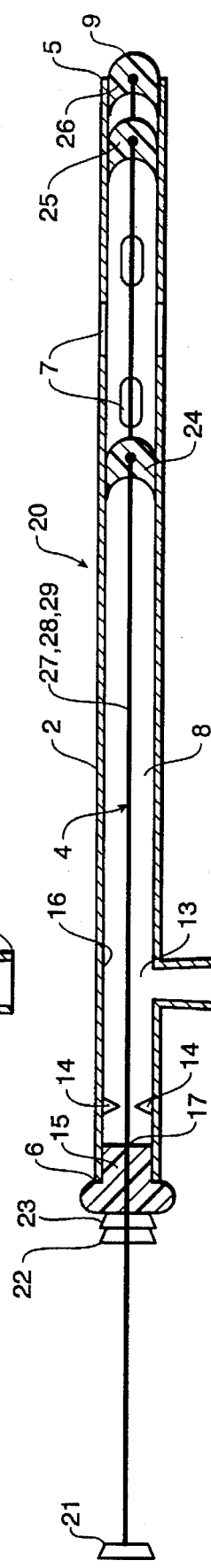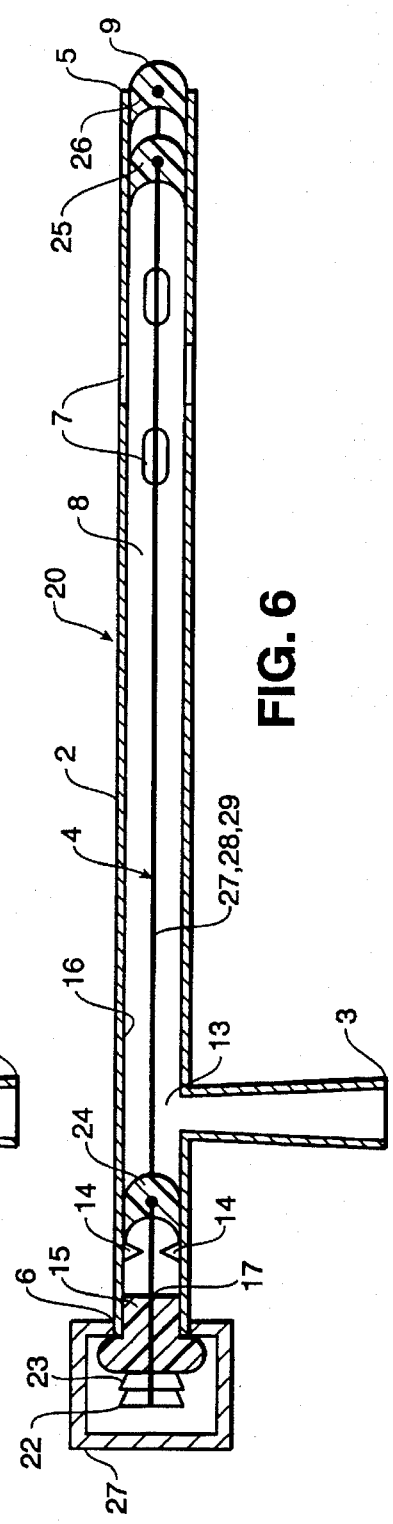

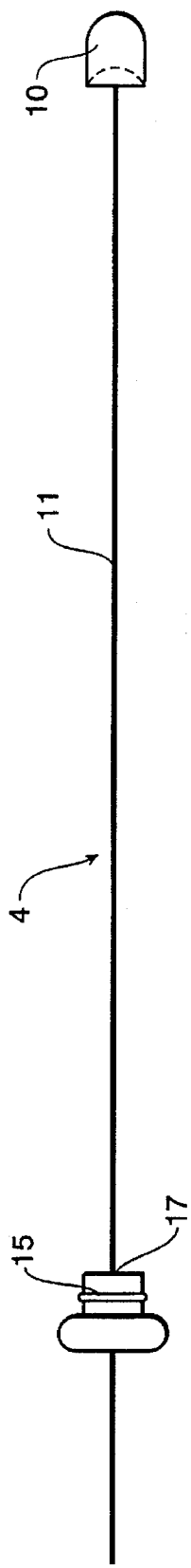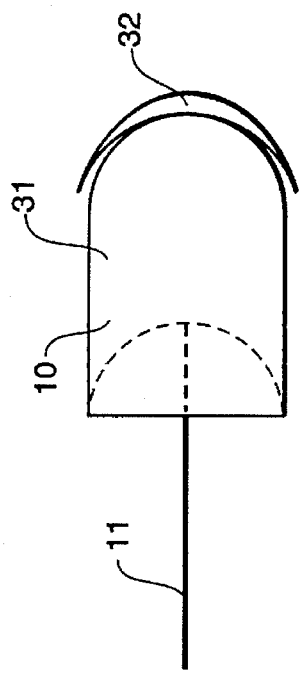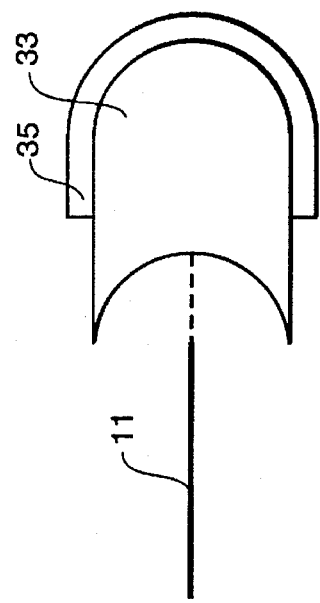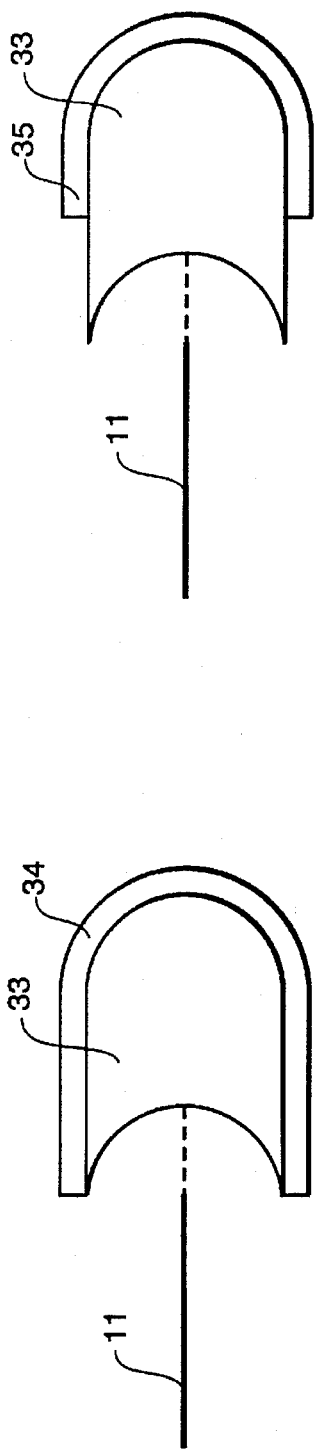
FIG. 7
FIG. 8
FIG. 10
FIG. 9

SURGICAL DRAIN

FIELD OF THE INVENTION

This application relates to the field of surgical devices, particularly surgical drains used to allow surgical wounds to drain and heal.

BACKGROUND

Surgical drains are used to drain fluids from a wound after surgery. Such drains generally comprise a tube having perforations in a wall of the tube. The perforated tube is placed in the wound to be drained, generally for a period of four to seven days. The tube is generally connected to a vacuum chamber or Vacuutainer (a device used to take blood samples) to help drain the wound. If the fluid being drained is blood, there may clotting around or blockage of the perforations in the tube, thereby limiting the drainage therethrough.

Also, when the drainage stops, it is sometimes difficult to determine whether the drain is blocked by clotted blood or excess tissue, or whether the site has stopped oozing. Therefore, a drain is needed which enables clots and excess tissue to be removed from the perforations and the inside (lumen) of the perforated tube.

SUMMARY OF THE INVENTION

A preferred embodiment of the present invention provides an improved drain used to drain wounds after surgery. It provides a novel drain so that blockages may be removed simply and easily, and helps medical personnel determine whether a wound has healed and is no longer draining or whether the drain is simply clogged.

A preferred embodiment comprises a tube-shaped drain with a plunger located within an inside cavity of the drain. The portion of the drain that is positioned within the human body has perforations that allow excess fluid to drain away from the wound. The plunger is used to scrape away clotted blood, excess tissue, and other debris which extends through, and may block the perforations of the device. The portion of the drain located outside the body is sealed so that a vacuum source may be attached to extract any debris dislodged by the plunger and to aid draining the wound. Alternatively, the wound may drain naturally through the drain without the use of a vacuum.

Accordingly, it is an object of the present invention to provide an improved surgical drain.

Another object of this invention is to provide an improved surgical drain which enables the removal of clogs, blockages or debris in the perforations and lumen of the drain.

Another object of this invention is to provide an improved surgical drain which enables medical personnel to more readily determine whether a wound has stopped draining or whether the drain is simply clogged or blocked.

BRIEF DESCRIPTION OF THE DRAWINGS

These and other objects of the present invention will become better understood through a consideration of the following description taken in conjunction with the drawings.

FIG. 4 is a cross-sectional view of a second embodiment of the present invention, showing multiple plungers in a drain.

FIG. 5 is a cross-sectional view of the embodiment of FIG. 4, showing multiple plungers in a drain with one plunger partially withdrawn from the drain.

FIG. 6 is a cross-sectional view of the embodiment of FIGS. 4 & 5, showing multiple plungers in a drain with one plunger substantially withdrawn from the drain.

FIG. 7 is a side view of a single plunger used in the embodiments shown in FIGS. 1–6.

FIG. 8 is an enlarged view of a scraper used in the embodiments shown in FIGS. 1–7.

FIG. 9 is a cross-sectional view of a scraper having a solid core with a foam skin covering the full length of the scraper.

FIG. 10 is a cross-sectional view of a scraper having a solid core with a foam skin covering half the length of the scraper.

DETAILED DESCRIPTION

Figure 1:
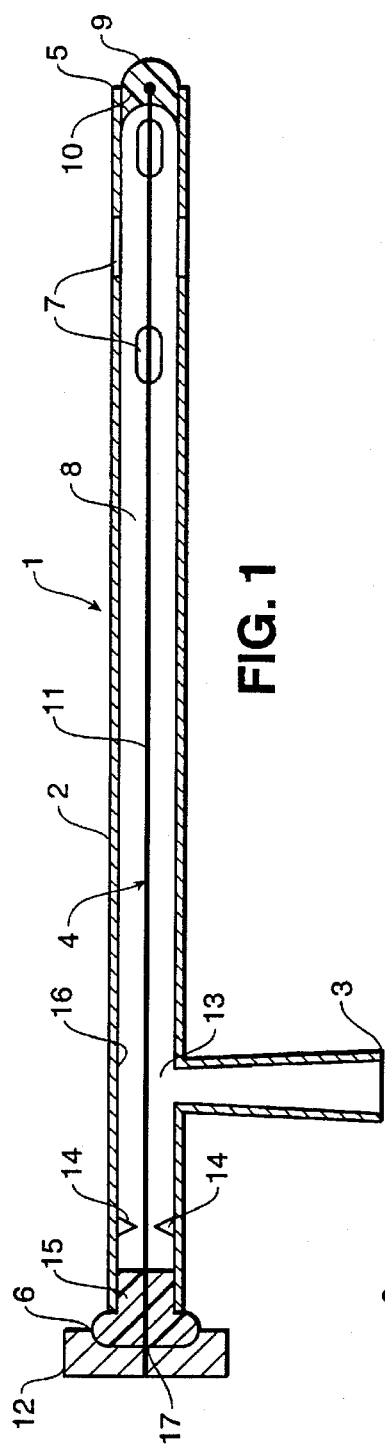
FIG. 1 is a cross-sectional view of a preferred embodiment of the present invention, showing a plunger located in a drain.

Turning now to the drawings in detail, FIG. 1 illustrates a preferred embodiment of a surgical drain 1 of the present invention. The drain 1 comprises a body 2 (preferably having a vacuum port 3) and a plunger 4.

The body 2 is generally in the shape of a tube forming a lumen 8 having a lumen inner surface 16. The body 2 includes a distal end 5 which ends in a tip 9 and a proximal end 6. The distal end 5 is generally placed inside a wound of a patient. The proximal end 6 generally remains outside the patient. Near the distal end 5, the body 2 includes a number of perforations 7 to allow excess fluids to flow from the wound into the lumen 8. The actual size of the drain may vary, and will generally include a range of 5 French to 50 French. The number and spacing of the perforations 7 may also vary depending on the size of the drain 1 used in the particular application. For example, for deep wounds, the drain may be larger, resulting in a larger number of perforations 7. The body 2 may be constructed from a wide selection of FDA-approved implantable materials such as plastics, including, among others, silicon and/or polyethylene. The tip 9 may include perforations and is generally rounded to allow for easier insertion into the wound and is shaped to fit the contours of the plunger 4.

The preferred drain 1 has a "T" junction 13 near the proximal end 6, where the vacuum port 3 extends from the body 2. The vacuum port 3 forms the base of the "T" and is shaped to attach to a vacuum chamber (not shown) or a Vacuutainer or any such device used to take blood samples or draw negative pressure. Near the proximal end 6 of the base 2 (the left side of FIG. 1) and preferably between the T junction 13 and the proximal end 6 is a shoulder 14 that extends axially around the inner circumference or perimeter of the lumen inner surface 16. The shoulder 14 can be integrally molded into the lumen inner surface 16 or fixedly attached by means well known in the art. As is explained below, the shoulder 14 acts to limit the range of motion of the plunger 4 so that the plunger 4 cannot be completely withdrawn from the drain 1. A diaphragm 15 is located at, and substantially seals the proximal end 6 of the drain. The diaphragm 15 is fixedly attached to the inner surface 16 by means known in the art, and is constructed of a pliable material such as rubber. The diaphragm 15 has a center hole 17 through which a plunger line 11 passes.

The plunger 4 comprises the plunger line 11 having a scraper 10 attached to one end of the line 11 and an integral plunger handle/cap 12 on the other end. The scraper 10 is generally positioned in the lumen 8 of the drain 1 and the plunger handle/cap 12 is generally positioned exterior the lumen 8. The scraper 10 is positioned at the distal end 5 of the drain 1 such that the perforations 7 of the drain 1 lie between the scraper 10 and the vacuum port 3. The line 11 may preferably be constructed using plastic, metal, or any other suitable material. The scraper 10 is preferably constructed of a material sufficiently rigid to withstand the force necessary to loosen any material or debris collected within the lumen 8. The scraper 10 is fixedly attached to one end of the plunger line 11 by means well known in the art. The line 11 passes through the center hole 17 of the diaphragm 15, and the opposite end of the line 11 is fixedly attached to the integral plunger handle/cap 12 by means well known in the art. The plunger handle/cap 12 is sized to fit over the proximal end 6 of the body 2 to substantially seal the drain 1 from outside air.

The surgical drain 1 may be used after surgery to drain fluids from a wound. The distal end 5 may be inserted into a wound to any depth necessary, generally determined by medical personnel. Preferably, no perforations should be exposed to outside air (i.e., extended out of the wound) during use of the drain. Fluids naturally flow from the outside of the drain 1 and through the perforations 7. Such fluids may be withdrawn through the vacuum port 3. Additionally, a vacuum source (not shown) can be attached to the vacuum port 3 to assist in withdrawing excess tissue, fluid, blood and other debris. The vacuum port 3 can be attached to a vacuum source either continuously or periodically as required.

Figure 2:
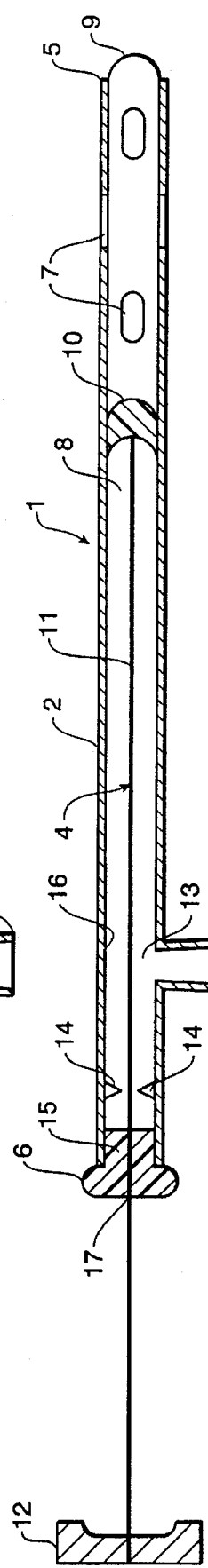
FIG. 2 is a cross-sectional view of the preferred embodiment of FIG. 1, showing the plunger partially withdrawn from the drain.

If fluid stops draining through the drain 1, this may be simply because the wound has stopped oozing or because the drain 1 (either the perforations 7 or the lumen 8) has clogged due to blood clotting therein or from debris or excess tissue getting caught therein. To remove a clog, an operator may pull the plunger handle/cap 12 off of and away from the proximal end 6, as illustrated in FIG. 2. As the handle/cap 12 is pulled, the line 11 is also pulled and causes the scraper 10 to be pulled through the lumen 8. The scraper 10 is sized to be just smaller than the diameter of the lumen 8, so that it scrapes away and collects excess tissue and clotted blood from inside the lumen 8. This allows the blood, tissue and other debris to be withdrawn out of the drain 1 through the vacuum port 3. The scraper 10 is pulled (to the left as shown in FIG. 2) past the T junction 13 until it contacts the shoulder 14. The shoulder 14 preferably prevents the scraper 10 from being removed from the drain 1.

Figure 3:
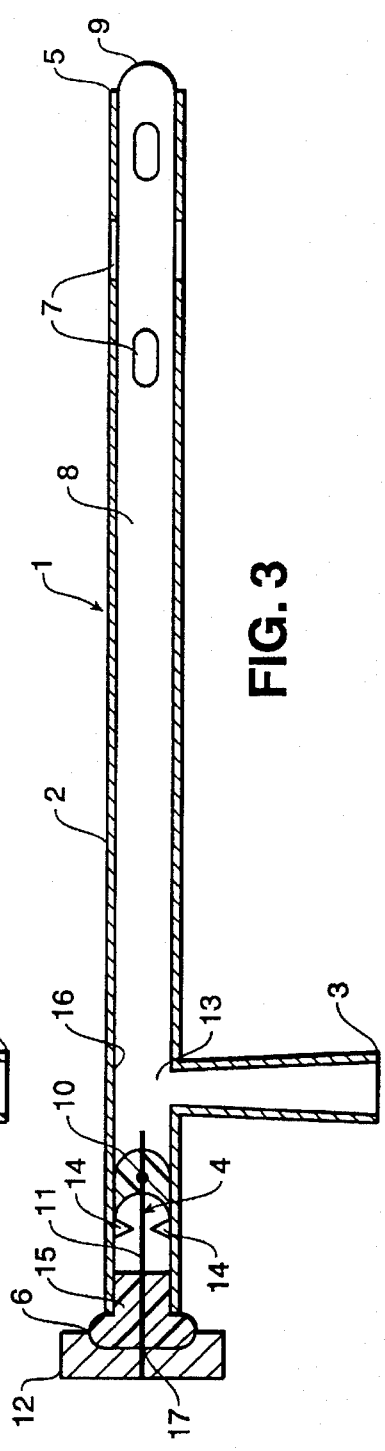
FIG. 3 is a cross-sectional view of the preferred embodiment of FIGS. 1 & 2, showing the plunger substantially withdrawn from the drain.

Once the scraper 10 has reached the shoulder 14, the line 11 may be cut so that the handle/cap 12 is detached therefrom. The handle/cap 12 may now be used solely as a cap 12, and may be placed back over the end 6 so that the drain 1 is once again sealed to outside air, as shown in FIG. 3.

When considering preferred materials for the scraper 10, it should be kept in mind that the inner diameter of the lumen 8 may vary due to sections of the drain 1 being exposed to different tolerance levels. For this reason, the scraper 10 is preferably made of a foam core 31 with a plastic disk 32 positioned behind the foam to provide rigidity (as illustrated in FIG. 8). One benefit of having a scraper 10 made of foam 31 with a plastic disk 32 is that the scraper 10 will conform to the size and shape of the lumen 8 as it is being pulled therethrough. Additional benefits of these materials are that they offer low resistance when the scraper 10 is being pulled through the lumen and will allow a suction to be maintain during scraping.

Alternative materials for the scraper 10 include solid materials with a slick coating such as Teflon™ (not shown). A scraper 10 made of a solid material would preferably be tapered in shape to reduce friction of the scraper 10 against the inner walls of the lumen 8 as the scraper 10 is being pulled therethrough. However, using a scraper 10 constructed solely of a solid material may not allow the scraper 10 to fit the lumen 8 consistently (i.e., the scraper may fit loosely in sections where the inner diameter of the lumen 8 is larger and tightly in areas where the inner diameter of the lumen 8 is smaller). In addition, when a scraper 10 made of a solid material is pulled through an inconsistently sized lumen 8, the pulling action may cause the entire drain 1 to snake or move back-and-forth. Such unnecessary movement is usually undesirable. Therefore, two alternatives are suggested. The first, illustrated in FIG. 9, uses a solid material core 33 with a foam skin 34. The second, illustrated in FIG. 10, uses a solid material core with a foam skin 35 that covers only a portion of the core 33. In either case, the foam skin 34 and 35 enables the scraper 10 to conform to the size and shape of the lumen 8 as it is being pulled therethrough, minimizing unnecessary movement of the drain 1.

In a second embodiment, the drain 20 includes the same features as described above except it is constructed with multiple scrapers 24, 25, and 26, as shown in FIG. 5. Multiple scrapers 24, 25, and 26 are positioned near the distal end 5, with lines 27, 28 and 29 individually attached to each. Each of these lines 27, 28 and 29 is attached to an individual handle 21, 22, or 23. Individual lines 27, 28 and 29 are not separately shown in FIGS. 4-6 because, although they individually extend through the lumen 8, they are all located substantially in the center of the lumen 8. However, the drain 20 includes a single, detachable cap 27, rather than the integral plunger handle/cap 12 described above. Each individual line 27, 28 and 29 connects to one scraper and one handle, as for example handle 21 connects to line 27 which connects to scraper 24. As shown in FIGS. 5 & 6, pulling handle 21 causes scraper 24 to move and scrape the inside of the drain 20. After the scraper 24 is pulled all the way to the shoulder 14, the handle 21 is cut off. Moving the handle 21 and scraper 24 does not disturb handles 22 & 23, scrapers 25 & 26, or lines 28 and 29 because the line 27 for handle 21 and scraper 24 runs though central holes in the other handles and lines 28 and 29 run through holes in scraper 24.

FIG. 5 shows the drain 20 with the cap 27 removed, to enable scraping the lumen 8 of the drain 20. Once scraping is finished, the cap 27 can then be placed over the outer end 6 to seal the system, as shown in FIG. 6. This sequence can then be repeated for each scraper until all have been used.

Although the preferred embodiments discussed above describe the use of drains with one or multiple plungers, different numbers of plungers may be used and still fall within the scope of this invention. While embodiments of the present invention have been shown and described, various modifications may be made without departing from the scope of the present invention, and all such modifications and equivalents are intended to be covered.

We claim:

1. A surgical drain for draining wounds comprising:

an elongated tube-like body forming a lumen and having proximal and distal ends, said body having a plurality of perforations therein, and at least one plunger comprising a scraper, a line, and a handle, said scraper originally positioned in the distal end and movable longitudinally from the distal end to the proximal end within said lumen, constructed of a core material with a disk attached thereto, said scraper being sufficiently rigid to withstand the force necessary to loosen any material or debris collected within said lumen, and sized to be just smaller than the diameter of said lumen, said line extending through said lumen and having a first end attached to said scraper and a second end attached to said handle, and said handle positioned near the proximal end of the body.

2. The surgical drain of claim 1 further comprising a vacuum port in the proximal end of the body.

3. The surgical drain of claim 1 further comprising a diaphragm attached to the proximal end of the body, said diaphragm having an aperture therethrough and said line extending through said aperture.

4. The surgical drain of claim 1 wherein the core of said scraper is constructed of foam, and the disk is plastic.

5. A surgical drain for draining wounds comprising:

an elongated tube-like body forming a lumen and having proximal and distal ends, said body having a plurality of perforations therein, and a plunger comprising a solid scraper, a line, and a handle, said solid scraper originally positioned in the distal end and movable longitudinally from the distal end to the proximal end within said lumen, said line extending through said lumen and having a first end attached to said scraper and a second end attached to said handle, and said handle positioned near the proximal end of the body.

6. The surgical drain of claim 5 wherein said solid scraper has a slick coating.

7. A surgical drain for draining wounds comprising:

an elongated tube-like body forming a lumen and having proximal and distal ends, said body having a plurality of perforations therein, a vacuum port in the proximal end, and a diaphragm attached to the proximal end, at least one plunger comprising a scraper, a line, and a handle, said scraper originally positioned in the distal end and movable longitudinally from the distal end to the proximal end within said lumen, constructed of a foam material with a plastic disk attached thereto, said scraper being sufficiently rigid to withstand the force necessary to loosen any material or debris collected within said lumen, and sized to be just smaller than the diameter of said lumen, said line extending through said lumen and having a first end attached to said scraper and a second end attached to said handle, and said handle positioned near the proximal end of the body.

* * * * *